United States Patent [19]

Kraas et al.

[11] 4,334,089
[45] Jun. 8, 1982

[54] SUBSTITUTED OXOCARBOXYLIC ACIDS, PROCESSES FOR THEIR PREPARATION, THEIR USE AND MEDICAMENTS CONTAINING THEM

[75] Inventors: Ekkehard Kraas, Krummesse; Horst Wolf, Constance, both of Fed. Rep. of Germany

[73] Assignee: Byk Gulden Lomberg Chemische Fabrik Gesellschaft, Constance, Fed. Rep. of Germany

[21] Appl. No.: 279,961
[22] PCT Filed: Oct. 31, 1980
[86] PCT No.: PCT/EP80/00123
§ 371 Date: Jun. 29, 1981
§ 102(e) Date: Jun. 29, 1981
[87] PCT Pub. No.: WO81/01285
PCT Pub. Date: May 14, 1981

[30] Foreign Application Priority Data

Oct. 31, 1979 [CH] Switzerland .................. 9785/79

[51] Int. Cl.³ .............................................. C07C 62/32
[52] U.S. Cl. .................. 562/463; 562/459; 260/408; 260/413; 260/415; 424/308; 424/317; 424/318; 560/51; 560/53
[58] Field of Search ............... 562/463, 459; 260/408, 260/413, 415; 424/308, 317, 318; 560/51, 53

[56] References Cited

U.S. PATENT DOCUMENTS 3,182,061 5/1965 Goldschmidt ................... 562/463
3,592,846 7/1971 Raymond ......................... 562/463
3,855,245 12/1974 Koyama et al. ................. 562/459
4,029,699 6/1977 Murata et al. ................... 562/463

FOREIGN PATENT DOCUMENTS 779821 2/1972 Belgium ............................ 562/459
2365755 8/1976 Fed. Rep. of Germany ...... 562/459
1016634 10/1976 Japan ................................ 562/459

OTHER PUBLICATIONS

Fieser, L. F. et al., JACS 58 (1936), pp. 2319-2322.

Primary Examiner—Paul J. Killos
Attorney, Agent, or Firm—Berman, Aisenberg & Platt

[57] ABSTRACT

Substituted oxocarboxylic acids of the formula I

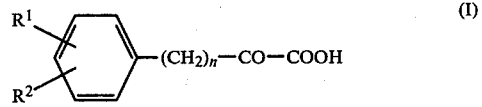

(I)

wherein
$R^1$ denotes a hydrogen atom, a halogen atom, a hydroxyl group, a lower alkyl group, a lower alkoxy group or a trifluoromethyl group,
$R^2$ denotes a hydrogen atom or a halogen atom and n denotes an integer from 3 to 8, and their salts display a hypoglycaemic action in warm-blooded animals. Processes for the preparation of the new compounds and of the intermediate products required for their preparation, as well as of the corresponding medicaments are described.

13 Claims, No Drawings

SUBSTITUTED OXOCARBOXYLIC ACIDS, PROCESSES FOR THEIR PREPARATION, THEIR USE AND MEDICAMENTS CONTAINING THEM

The invention relates to substituted oxocarboxylic acids, processes for their preparation, their use and medicaments containing them.

α-Keto-acid esters which can be used as intermediate products for the preparation of aminoacids or heterocyclic compounds are described in German Offenlegungsschrift No. 2,365,755. A process for the preparation of α-keto-acids is known from Belgian Pat. No. 779,821, the keto-acids being mentioned as intermediate products in metabolism or as precursors of aminoacids. 5-(4-Methoxyphenyl)-2-oxovaleric acid has been prepared by L. F. Fieser and H. L. Holmes [J. Amer. Chem. Soc. 58(1936)2319]. Certain substituted oxocarboxylic acids have now been discovered as pharmaceutical active compounds with a specific action.

The invention relates to substituted oxocarboxylic acids of the general formula I

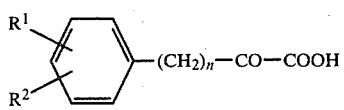 (I)

wherein
R$^1$ denotes a hydrogen atom, a halogen atom, a hydroxyl group, a lower alkyl group, a lower alkoxy group or a trifluoromethyl group,
R$^2$ denotes a hydrogen atom or a halogen atom and n denotes an integer from 3 to 8,
excluding those wherein
R$^1$ denotes a hydrogen atom or a methoxy group and R$^2$ denotes a hydrogen atom, if
n denotes 3,
and their salts.

Possible lower alkyl groups are straight-chain or branched alkyl radicals with 1 to 4 carbon atoms. Examples of straight-chain alkyl radicals are the methyl, ethyl, n-propyl and n-butyl radical, of which those with 1 and 2 carbon atoms are preferred. Examples of branched alkyl radicals are the isopropyl, isobutyl and sec.-butyl radical, of which the radical with 3 carbon atoms is preferred. Possible alkyl radicals in lower alkoxy groups are both straight-chain and branched lower alkyl groups. The methoxy group is the preferred lower alkoxy group.

Halogen atoms are fluorine, chlorine and bromine atoms, of which fluorine and, in particular, chlorine are preferred.

The substituents R$^1$ and R$^2$ are preferably in the meta-position or para-position to the ketocarboxylic acid radical.

Possible salts are salts with inorganic and organic bases. Pharmacologically unacceptable salts are converted into pharmacologically, that is to say biologically, acceptable salts, which are the preferred salts according to the invention, by methods which are known per se. Above all cations of alkali metals, alkaline earth metals or earth metals are used as cations for the salt formation, but cations corresponding to organic nitrogen bases, such as amines, aminoalkanols, aminosugars, basic aminoacids and the like, can also be used.

Examples which may be mentioned are the salts of ethylenediamine, dimethylamine, diethylamine, morpholine, piperidine, piperazine, N-lower alkyl-piperazine (for example N-methylpiperazine), methylcyclohexylamine, benzylamine, ethanolamine, diethanolamine, triethanolamine, tris-(hydroxymethyl)-aminomethane, 2-amino-2-methylpropanol, 2-amino-2-methyl-1,3-propanediol, glucamine, N-methylglucamine, glucosamine, N-methylglucosamine, lysine, ornithine, arginine and quinoline and preferably of lithium, sodium, potassium, magnesium, calcium and aluminium.

Substituted oxocarboxylic acids of the general formula I*

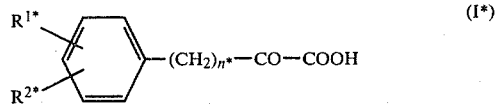 (I*)

wherein
R$^{1*}$ denotes a hydrogen atom, a chlorine atom, a methyl group, a methoxy group or a trifluoromethyl group,
R$^{2*}$ denotes a hydrogen atom or a chlorine atom and
n* denotes an integer from 3 to 6,
excluding those wherein
R$^{1*}$ denotes a hydrogen atom or a methoxy group, and R$^{2*}$ denotes a hydrogen atom, if
n* denotes 3,
and salts thereof form an embodiment of the invention.

Substituted oxocarboxylic acids of the general formula I**

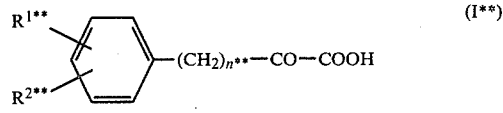 (I**)

wherein
R$^{1}$ and R$^{2}$ are in the meta-position or para-position to the ketocarboxylic acid radical, and
R$^{1**}$ denotes a hydrogen atom or a chlorine atom,
R$^{2**}$ denotes a chlorine atom and
n** denotes 3 to 5,
and their pharmacologically acceptable salts with inorganic or organic bases form a preferred embodiment of the invention.

Examples which may be mentioned of representatives of the acids according to the invention are 6-(2,4-dichlorophenyl)-2-oxocaproic acid, 2-oxo-6-(3-trifluoromethylphenyl)-caproic acid, 5-(3,4-dichlorophenyl)-2-oxovaleric acid, 7-(3-chlorophenyl)-2-oxoheptanoic acid, 7-(4-methoxyphenyl)-2-oxoheptanoic acid, 7-(4-bromophenyl)-2-oxoheptanoic acid, 8-(4-n-butoxyphenyl)-2-oxo-octanoic acid, 8-(3-fluorophenyl)-2-oxooctanoic acid, 2-oxo-8-(3-trifluoromethylphenyl)-octanoic acid, 7-(4-methylphenyl)-2-oxo-heptanoic acid, 8-(4-hydroxyphenyl)-2-oxo-octanoic acid, 9-(4-chlorophenyl)-2-oxo-nonanoic acid, 9-(3-trifluoromethylphenyl)-2-oxo-nonanoic acid, 10-(2,4-dichlorophenyl)-2-oxo-decanoic acid and 10-(4-methylphenyl)-2-oxo-decanoic acid.

Preferred representatives are 2-oxo-6-phenylcaproic acid, 6-(4-methoxyphenyl)-2-oxo-caproic acid and 5-(4-chlorophenyl)-2-oxo-valeric acid, and their pharmacologically acceptable salts.

The compounds according to the invention have valuable pharmacological properties which render them commercially useful. They have a hypoglycaemic action.

Because of their advantageous activity, the substituted oxocarboxylic acids according to the invention, of the general formula I and I' and of embodiments I* and I**, and their salts are suitable for the treatment and prophylaxis of illnesses based on disorders in glucose metabolism. For example, prediabetic conditions are treated in order to prevent the manifestation of diabetes, manifest diabetes, for example diabetes in adults, and labile diabetes in young persons.

The invention thus also relates to a method for combating the illnesses mentioned by administration of the compounds according to the invention. The invention furthermore relates to the use of the compounds according to the invention in combating the illnesses mentioned.

The invention also relates to medicaments which contain one or more of the substituted oxocarboxylic acids of the general formula I'

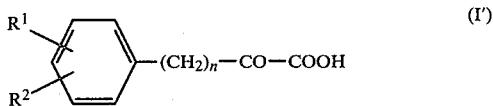

wherein
$R^1$ denotes a hydrogen atom, a halogen atom, a hydroxyl group, a lower alkyl group, a lower alkoxy group or a trifluoromethyl group,
$R^2$ denotes a hydrogen atom or a halogen atom and
n denotes an integer from 3 to 8,
and/or their pharmacologically acceptable salts with inorganic or organic bases.

Embodiments of the medicaments are those which contain substituted oxocarboxylic acids of the formula I', wherein $R^1$ denotes a hydrogen atom, a chlorine atom, a methyl group, a methoxy group or a trifluoromethyl group, $R^2$ denotes a hydrogen atom or a chlorine atom and n denotes an integer from 3 to 6, I* or I**, or the pharmacologically acceptable salts of the acids with inorganic or organic bases.

The invention furthermore relates to the use of the compounds according to the invention for the preparation of medicaments for combating the illnesses mentioned.

The medicaments are prepared by processes which are known per se. As medicaments, the new compounds can be employed as such or, if appropriate, in combination with suitable pharmaceutical excipients. If the new pharmaceutical formulations contain pharmaceutical excipients in addition to the active compounds, the content of active compound in these mixtures is 1 to 95, preferably 15 to 85, percent by weight of the total mixture.

In accordance with the invention, the active compounds can be used, in the field of human medicine, in any desired form, for example systemically, provided that the establishment and maintenance of sufficient levels of active compounds in the blood or tissue are ensured. This can be achieved, for example, by oral or parenteral administration in suitable doses. The pharmaceutical formulation of the active compound is advantageously in the form of unit doses appropriate for the desired administration. A unit dose can be, for example, a tablet, a dragee, a capsule, a suppository or a measured volume of a powder, of a granular material, of a solution, of an emulsion or of a suspension.

"Unit dose" for the purpose of the present invention means a physically determined unit which contains an individual amount of the active constituent in combination with a pharmaceutical excipient, the content of active compound in the unit dose corresponding to a fraction or multiple of a therapeutic individual dose. An individual dose preferably contains the amount of active compound which is given in one administration and usually corresponds to a whole daily dose or a half, one-third or one-quarter of the daily dose. If only a fraction, such as a half or one-quarter, of the unit dose is required for an individual therapeutic administration, the unit dose is advantageously divisible, for example in the form of a tablet with a breaking groove.

When in the form of unit doses and intended, for example, for administration to humans, the pharmaceutical formulations according to the invention contain about 2 to 200 mg, advantageously 10 to 100 mg and in particular 20 to 60 mg, of active compound.

In general, it has proved advantageous in human medicine to administer the active compound or compounds, when these are given orally, in a daily dose of about 0.1 to about 30, preferably 0.3 to 15 and in particular 0.6 to 3 mg/kg of body weight, if appropriate in the form of several, preferably 1 to 3, individual administrations to achieve the desired results. An individual administration contains the active compound or compounds in amounts of about 0.05 to about 10, preferably 0.1 to 5 and in particular 0.3 to 1 mg/kg of body weight.

Similar dosages can be used in the case of parenteral treatment, for example intravenous or intramuscular administration. About 0.3 to 1 mg of active compound/kg of body weight is administered in this therapy.

In the case of long-term medication, therapeutic administration of the pharmaceutical formulation in general takes place at fixed points in time, such as 1 to 4 times daily, for example after each meal and/or in the evening. In acute cases, medication takes place at varying points in time. Under certain circumstances, it may be necessary to deviate from the dosages mentioned, and in particular to do so in accordance with the nature, body weight and age of the individual to be treated, the nature and severity of the illness, the nature of the formulation and of the administration of the medicament, and the time or interval over which administration takes place. Thus it can in some cases be sufficient to manage with less than the abovementioned amount of active compound, whilst in other cases the abovementioned amount of active compound must be exceeded. The optimum dosage and method of administration of the active compounds required in each particular case can be determined by the expert on the basis of his expert knowledge.

The pharmaceutical formulations as a rule consist of the active compounds according to the invention and non-toxic, pharmaceutically acceptable medicinal excipients, which are used as an admixture or diluent in solid, semi-solid or liquid form, or as a means of encasing, for example in the form of a capsule, a tablet coating, a sachet or some other container for the therapeutically active constituent. An excipient can, for example, serve as a promoter of the resorption of the medicament by the body, as a formulating auxiliary, as a sweetener, as a flavour correctant, as a colorant or as a preservative.

Examples of forms which may be used orally are tablets, dragees, hard and soft capsules, for example made of gelatin, dispersible powders, granules, aqueous and oily suspensions, emulsions or solutions.

Tablets may contain inert diluents, for example calcium carbonate, calcium phosphate, sodium phosphate or xylitol; granulating agents and dispersing agents, for example calcium phosphate or alginates; binders, for example starch, gelatin or gum acacia; and lubricants, for example aluminium stearate or magnesium stearate, talc or silicone oil. The tablets may additionally be provided with a coating, which can also be such that delayed dissolution and resorption of the medicament in the gastrointestinal tract and hence, for example, better toleration, a protracted effect or a retarded effect are achieved. Gelatin capsules may contain the medicament mixed with a solid diluent, for example calcium carbonate or kaolin, or an oily diluent, for example paraffin oil.

Aqueous suspensions may contain suspending agents, for example sodium carboxymethylcellulose, methylcellulose, hydroxypropylcellulose, sodium alginate, polyvinylpyrrolidone, gum tragacanth or gum acacia; dispersing agents and wetting agents, for example polyoxyethylene stearate, heptadecaethyleneoxycetanol, polyoxyethylene sorbitol monooleate, polyoxyethylene sorbitane monooleate, or lecithin; preservatives, for example methyl hydroxybenzoate or propyl hydroxybenzoate; flavouring agents; and sweeteners, for example saccharin or sodium cyclamate.

Oily suspensions may contain, for example, paraffin oil and thickeners, such as beeswax, hard paraffin or cetyl alcohol; and furthermore sweeteners, flavouring agents and antioxidants.

Water-dispersible powders and granules may contain the medicaments mixed with dispersing agents, wetting agents and suspending agents, for example those mentioned above, as well as with sweeteners, flavouring agents and colorants.

Emulsions may contain, for example, paraffin oil, in addition to emulsifying agents, such as gum acacia, gum tragacanth, phosphatides, sorbitane monooleate or polyoxyethylene sorbitane monooleate, and sweeteners and flavouring agents.

Sterile injectable aqueous suspensions, isotonic salt solutions or other solutions which may contain dispersing agents or wetting agents and/or pharmacologically acceptable diluents, for example propylene glycol or butylene glycol, are used for parenteral administration of the medicaments.

The active compound or compounds can also be formulated in a micro-encapsulated form, if appropriate together with one or more of the abovementioned excipients or additives.

In addition to the substituted oxocarboxylic acids according to the invention, in which the substituents have the abovementioned meaning, and/or their salts, the pharmaceutical formulations can also contain one or more pharmacologically active constituents of other groups of medicaments, such as antidiabetic agents (sulphonamides, sulphonylureas and the like), for example carbutamide, tolbutamide, chlorpropamide, glibenclamide, glibornuride, glisoxepide, gliquidone and glymidine, or hypolipidaemic agents, such as nicotinic acid and derivatives and salts thereof.

The invention also relates to a process for the preparation of the substituted oxocarboxylic acids of the general formula I

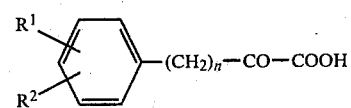

wherein
$R^1$ denotes a hydrogen atom, a halogen atom, a hydroxyl group, a lower alkyl group, a lower alkoxy group or a trifluoromethyl group,
$R^2$ denotes a hydrogen atom or a halogen atom and
n denotes an integer from 3 to 8,
excluding those wherein
$R^1$ denotes a hydrogen atom or a methoxy group and
$R^2$ denotes a hydrogen atom, if
n denotes 3,
and their salts, characterised in that (a) an oxocarboxylic acid ester of the general formula II

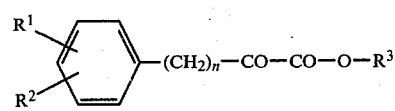

wherein
$R^1$, $R^2$ and n have the abovementioned meaning and
$R^3$ denotes a lower alkyl radical,
is solvolysed and, if appropriate, resulting acids are subsequently converted into the salts or resulting salts are subsequently converted into the acids, or (b) a diester of the general formula III

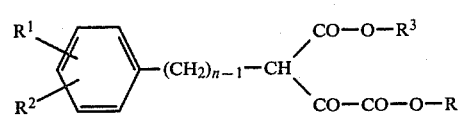

wherein
$R^1$, $R^2$, $R^3$ and n have the abovementioned meaning,
is solvolysed and decarboxylated, and, if appropriate, resulting acids are subsequently converted into the salts or resulting salts are subsequently converted into the acids.

The compounds of the general formula I are prepared by processes which are known per se. As well as by the process variants mentioned, the compounds I can also be prepared by processes analogous to other processes described in the literature, examples which may be mentioned being: the methods given in Belgian Pat. No. 779,821, and the processes of H. Poisel [Ber. 111 (1978) 3136], R. Fischer and T. Wieland [Ber. 93 (1960) 1387], J. Anatol and A. Medète [Synthesis 1971, 538], E. E. Eliel and A. A. Hartmann [J.org.Chem. 37 (1972) 505], K. Tanaka et al. [Tetrahedron Letters 1978, 4809] and K. Ogura et al. [Tetrahedron Letters 1978, 375].

The oxocarboxylic acid esters II and the diesters III are solvolysed, for example, with an aqueous or alcoholic (for example ethanolic) alkali metal hydroxide (for example potassium hydroxide) solution at room temperature, an inert diluent, such as dioxane or toluene, being added if appropriate. The solvolysis is preferably carried out with aqueous solutions of mineral acids, such as hydrochloric acid, hydrobromic acid or sulphuric acid, if appropriate with the addition of an organic solvent, such as dioxane or diglyme, at temperatures between 0° C. and the boiling point of the solvent, preferably between 20° and 70° C. The decarboxylation of the diesters III is effected by heating the particular solutions, if appropriate at the same time as carrying out the solvolysis.

The oxocarboxylic acids of the general formula I and of embodiments I* and I** can be converted into the salts by direct alkaline solvolysis, for example hydrolysis, of the esters II ($R^3$=lower alkyl). The inorganic or organic base of which the salt is desired is used as the alkaline reactant. The salts are also obtained, however, if the acids I are reacted with the stoichiometrically equivalent amount of the corresponding base, for example sodium hydroxide or sodium ethanolate, or if readily soluble salts are converted into sparingly soluble salts by double decomposition, or if various salts are converted into pharmacologically acceptable salts. The preparation of the free oxo-acids I is preferable to the preparation of the salts.

Oxocarboxylic acid esters of the general formulae II* and II** or diesters III* and III**

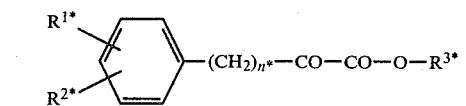  (II*)

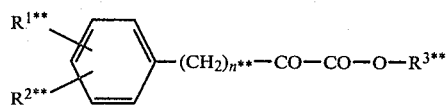  (II**)

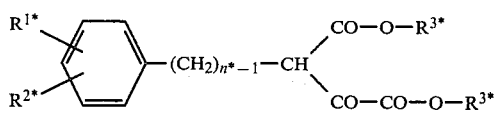  (III*)

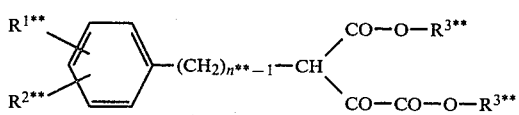  (III**)

wherein
$R^{1*}$, $R^{2*}$ and $n^*$ and $R^{1}$, $R^{2}$ and $n^{**}$ have the abovementioned meaning,
$R^{3*}$ denotes a lower alkyl radical and
$R^{3**}$ denotes a methyl or ethyl radical,
are employed for the preparation of the substituted oxocarboxylic acids of embodiments I* and I**.

The oxocarboxylic acid esters of the general formulae II, II* and II** are prepared by processes which are known per se, for example according to German Offenlegungsschrift No. 2,365,755. They can also be prepared by ozonolysis of α-methylenecarboxylic acid esters of the general formula IV

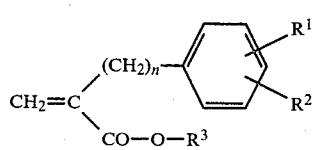  (IV)

wherein
$R^1$, $R^2$, $R^3$ and n have the abovementioned meaning.
The α-methylenecarboxylic acid esters IV (or the corresponding embodiments IV* and IV**) are prepared by methods analogous to the methods described by H. Stetter and H. Kuhlmann [Synthesis 1978, 29], Ph.E. Pfeffer et al. [J.Org.Chem. 37 (1972)1256] and W. S. Wadsworth, jun. and W. D. Emmons [J.Amer.Chem.Soc. 83 (1961) 1733].

The diesters III are prepared by methods customary to the expert, for example by reacting carboxylic acid esters V with a dialkyl oxalate VI

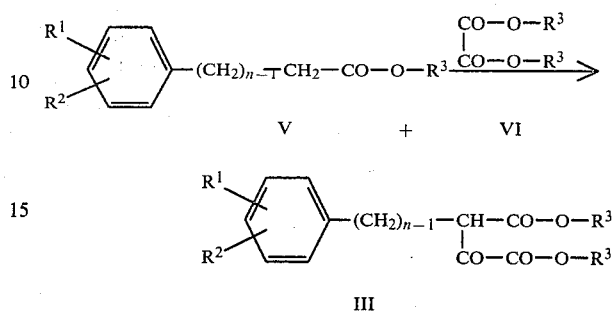

wherein
$R^1$, $R^2$, $R^3$ and n have the abovementioned meaning, in the presence of a strong base, for example sodium ethanolate or potassium tert.-butylate. The carboxylic acid esters V are obtainable by known methods, for example as described by R. Huisgen et al., Liebigs Annalen 586 (1954), 52.

The following examples serve to illustrate the invention without limiting it. B.p. denotes boiling point, m. denotes melting point and the temperature data are in °C.

EXAMPLES

EXAMPLE 1

2-Oxo-6-phenylcaproic acid (a) 10.0 g of the diester obtained according to (b) are heated to about 100° C. together with 100 ml of 6 N hydrochloric acid and 100 ml of dioxane for 4 hours. After cooling the mixture, it is diluted with 1.2 l of water and extracted several times with methylene chloride. The organic phase is washed with water and saturated sodium chloride solution and then dried and concentrated. The oily residue is purified by high vacuum distillation (b.p.: 130°–135° C. under 0.1 mm Hg [13.3 Pa]) and column chromatography (mobile phase: chloroform). 2.9 g of 2-oxo-6-phenylcaproic acid remain as an oil which does not crystallise, yield: 43% (of theory).

(b) 47.9 g of 5-phenylvaleric acid ethyl ester are added to a sodium ethylate suspension, prepared from 6.4 g of sodium and 100 ml of ethanol with subsequent evaporation of excess ethanol and addition of 100 ml of toluene. 44.1 g of diethyl oxalate are added dropwise, whilst stirring, and the mixture is heated under reflux for 2.5 hours. After cooling, the solution is stirred with 500 ml of ice-water and the mixture is acidified to pH 2 with 2 N sulphuric acid. Extraction several times with methylene chloride gives, after drying, filtration through a short silica gel column and concentration, 62.1 g of 3-ethoxycarbonyl-2-oxo-6-phenylhexanoic acid ethyl ester, which is reacted according to (a), without further purification.

EXAMPLE 2

6-(4-Methoxyphenyl)-2-oxocaproic acid (a) The diester obtained according to (b) is hydrolysed and decarboxylated in a manner analogous to that in Example (1a), using 6 N hydrochloric acid. The methylene chloride extracts collected are concentrated, the residue is dissolved in diethyl ether and the solution is extracted several times with 1 N sodium hydroxide solution. The aqueous phases are acidified to pH 5.5 with 6 N hydrochloric acid and washed three times with diethyl ether. The aqueous phase is then brought to pH 1-2 and extracted with methylene chloride. After drying and concentration, a viscous oil remains, which crystallises in the cold from petroleum ether (50°-70° C.). Yield: 6.2 g (51% of theory), m.: 22°-25°.

(b) 17.2 g of 3-ethoxycarbonyl-6-(4-methoxyphenyl)-2-oxocaproic acid ethyl ester are prepared from 14.7 g of 5-(4-methoxyphenyl)-valeric acid ethyl ester and 11.8 g of diethyl oxalate, using sodium ethylate as the base, in a manner analogous to that in Example (1b).

EXAMPLE 3

5-(4-Chlorophenyl)-2-oxovaleric acid (a) 5-(4-Chlorophenyl)-2-oxovaleric acid ethyl ester (residue from b) is taken up in 100 ml of 6 N hydrochloric acid and 100 ml of dioxane and the mixture is heated to 100° for 3 hours. After cooling, it is diluted with 1 l of water and extracted several times with methylene chloride. The organic phase is washed several times with water, dried over magnesium sulphate and concentrated. The residue is subjected to high vacuum distillation in a bulb-tube oven and the product is recrystallised from petroleum ether. 5.7 g of the title compound of m. 82°-84° are obtained.

(b) 14 g of 5-(4-chlorophenyl)-2-methylenevaleric acid ethyl ester are dissolved in 350 ml of ethanol and treated with the equivalent amount of ozone. After flushing the apparatus with nitrogen, about 1 g of palladium-on-charcoal (10% of Pd) is added and the ozonide formed is reduced with hydrogen in a circulatory process. The catalyst is then filtered off and the solution is concentrated in vacuo.

(c) 53.3 g of 5-(4-chlorophenyl)-2-methylenevaleric acid ethyl ester of b.p. 120°-123° under 0.05 mm Hg (6.65 Pa) are obtained from 71 g of 3-(4-chlorophenyl)-propylmalonic acid monoethyl ester, 10.42 g of paraformaldehyde, 47 ml of pyridine and 3.1 ml of piperidine by a method analogous to that described by H. Stetter and H. Kuhlmann [Synthesis 1979, 29].

(d) A solution of 16.8 g of potassium hydroxide in 400 ml of ethanol is added dropwise to 92 g of 3-(4-chlorophenyl)-propylmalonic acid diethyl ester in 200 ml of ethanol at room temperature. The mixture is stirred for 24 hours and substantially concentrated in vacuo, the residue is taken up in 500 ml of water and the mixture is extracted twice with 100 ml of diethyl ether each time. The aqueous phase is acidified with concentrated hydrochloric acid, whilst cooling with ice, and extracted 3 times with 200 ml of diethyl ether each time, and, after drying over sodium sulphate, the organic phase is concentrated. 71.8 g of 3-(4-chlorophenyl)-propylmalonic acid ethyl ester remain as a viscous oil.

(e) 108.5 g of malonic acid diethyl ester are added dropwise, at 50°, to a sodium ethylate solution freshly prepared from 15.6 g of sodium and 750 ml of ethanol. The mixture is kept at the above temperature for 2.5 hours and 220 g of p-toluenesulphonic acid 3-(4-chlorophenyl)-propyl ester are then added dropwise. After the addition, the mixture is stirred at 50° for 6 hours, 800 ml of water are then added and the mixture is extracted 3 times with a total of 1 liter of diethyl ether. The combined organic phases are dried over sodium sulphate, the solvent is evaporated off and the residue is distilled. 105.6 g of 3-(4-chlorophenyl)-propylmalonic acid diethyl ester of b.p. 145°-155° under 0.01 mm Hg (1.33 Pa) are obtained.

(f) 135 ml of pyridine are added dropwise to 150 g of 3-(4-chlorophenyl)-propan-1-ol and 206.6 g of p-toluenesulphonyl chloride in 300 ml of chloroform at 0°. After the addition, the mixture is stirred at room temperature for 3 hours and the solution is poured into a mixture of 400 ml of water and 120 ml of concentrated hydrochloric acid. The organic phase is separated off, washed 3 times with water, dried over sodium sulphate and concentrated to a yellowish viscous oil in vacuo, yield: 285 g of p-toluenesulphonic acid 3-(4-chlorophenyl)-propyl ester.

EXAMPLE 4

2-Oxo-7-(3-trifluoromethylphenyl)-heptanoic acid (a) The diester obtained according to (b) is hydrolysed and decarboxylated in a manner analogous to that in Example (1a), using 6 N hydrochloric acid in dioxane at 100°. After working up by extraction and purification by bulb tube distillation, 5.6 g of the title compound are obtained as a viscous, colourless oil which does not crystallise.

(b) 3-Ethoxycarbonyl-2-oxo-7-(3-trifluoromethylphenyl)-heptanoic acid ethyl ester is obtained in a yield of 11.7 g (80% of theory) from 10.9 g of 6-(3-trifluoromethylphenyl)-caproic acid ethyl ester and 6 g of diethyl oxalate with sodium ethylate as the base, in a manner analogous to that in Example (1b).

(c) 11.4 g of 6-(3-trifluoromethylphenyl)-caproci acid are dissolved in 200 ml of ethanol and, after adding 2 ml of concentrated sulphuric acid, the mixture is heated under reflux for 6 hours. After distilling off most of the solvent, water is added and the mixture is extracted with methylene chloride. Treatment with sodium bicarbonate solution and drying and concentrating gives 12.6 g of the corresponding ethyl ester as an oil which is used in (b) without further purification.

(d) 24.9 g of 4-(3-trifluoromethylphenyl)-butylmalonic acid diethyl ester are heated under reflux with 4.5 g of potassium hydroxide in 200 ml of toluene: methanol (2:1) for 36 hours and the mixture is then subjected to acid extraction. The residue which remains after drying and concentrating is heated to about 170° in vacuo for 2 hours; carbon dioxide is thereby liberated and the corresponding caproic acid, which is used in (c), is formed.

(e) 5.5 g of oxirane in 20 ml of diethyl ether are added dropwise, at about 0° C., to a Grignard solution prepared from 28.5 g of 2-(3-trifluoromethylphenyl)-ethyl bromide and 2.9 g of magnesium in 200 ml of diethyl ether. After stirring the mixture for 1 hour and adding 100 ml of 10% strength sulphuric acid, it is extracted with diethyl ether and the residue is distilled. About 18.5 g of 4-(3-trifluoromethylphenyl)-butan-1-ol are obtained and are dissolved in 70 ml of toluene, 16 g of p-toluenesulphonyl chloride and 25 ml of pyridine are added and the mixture is stirred. After 2 days, the precipitate is filtered off and worked up by extraction. After concentrating the organic phase, 25.7 g of the tosylate of the substituted butanol remain and are taken up in 250 ml of ethanol and the mixture is added dropwise to a solution prepared from 11.5 g of diethyl malonate and 1.6 g of sodium in 220 ml of absolute ethanol. The mixture is heated under reflux for 24 hours and then concentrated and the residue is partitioned between water and methylene chloride. After several extractions, the organic phases collected are dried and concentrated. The residue is purified by chromatography over a 500 g silica gel column and gives 24.9 g of 4-(3-trifluoromethylphenyl)-butylmalonic acid diethyl ester, which is used in (d).

EXAMPLE 5

9-(2,4-Dimethylphenyl)-2-oxo-nonanoic acid (a) 8.6 g of the diester obtained according to (b) are hydrolysed, and decarboxylated, with 6 N hydrochloric acid and dioxane, in accordance with the method mentioned in Example (1a). Extraction with methylene chloride, followed by washing, drying and concentrating, gives, after purification of the product by high vacuum distillation, 4.9 g of the title compound, in the form of a viscous oil.

(b) 7.5 g of the octanoic acid ester obtained according to (c) are reacted, analogously to Example (1b), with sodium ethylate and diethyl oxalate. After acidifying, extracting with methylene chloride, drying the extract and filtering it through silica gel, and removing the solvent, 8.6 g of 9-(2,4-dimethylphenyl)-3-ethoxycarbonyl-2-oxo-nonanoic acid ethyl ester are left.

(c) 12.8 g of 8-(2,4-dimethylphenyl)-7-oxo-octanoic acid ethyl ester [obtained according to (d)] are reduced, analogously to the method described by Huisgen [R. Huisgen et al., Liebigs Ann. 586 (1954), 52] with hydrazine hydrate in diethylene glycol. The isolated reduction product, in 200 ml of ethanol and 5 ml of concentrated sulphuric acid, is heated at the reflux temperature overnight and, after customary working up, gives 7.5 g of 8-(2,4-dimethylphenyl)-octanoic acid ethyl ester as a colourless oil.

(d) 14.5 g of 2,4-dimethylbenzyl bromide, magnesium and cadmium chloride are used to prepare the corresponding cadmium-dialkyl by Huisgen's method. This compound is then reacted, in benzene solution at the boil, with 11.2 g of pimelic acid ethyl ester chloride. Sulphuric acid is added to the mixture, the organic phase is washed and the benzene is evaporated off. The residue is distilled in a high vacuum, giving 12.8 g of 8-(2,4-dimethylphenyl)-7-oxo-octanoic acid ethyl ester.

EXAMPLE 6

10-(4-Chlorophenyl)-2-oxo-decanoic acid (a) 5.7 g of the diester obtained according to (b) are hydrolysed, and decarboxylated, with 6 N hydrochloric acid in dioxane, in accordance with Example (1a). After working up and purification by column chromatography, 3.8 g of the title compound remain as a colourless oil.

(b) 5.3 g of the compound obtained according to (c) are reacted with diethyl oxalate and sodium ethylate in accordance with Example (1b). Working up, and purification by filtration through silica gel, gives, after evaporation of the solvent, 5.7 g of 10-(2,4-dimethylphenyl)-3-ethoxycarbonyl-2-oxo-decanoic acid ethyl ester.

(c) 8.3 g of 9-(4-chlorophenyl)-9-oxo-nonanoic acid ethyl ester [obtained according to (d)] are reduced with hydrazine hydrate, and worked up, analogously to Example (5c). 5.3 g of 9-(4-chlorophenyl)-nonanoic acid ethyl ester are obtained as an oil.

(d) Using the method described by Papa et al. [J. Amer.Chem.Soc. 69 (1947), 3018], 12.3 g of azelaic acid ethyl ester chloride in 20 ml of chlorobenzene are mixed cold with 9.5 g of aluminium trichloride and the mixture is then heated at 150° overnight. After adding dilute hydrochloric acid to the complex, the organic phase is washed and concentrated; the residue is extracted with diethyl ether. After column chromatography, and concentration of the solution, 8.3 g of 9-(4-chlorophenyl)-9-oxo-nonanoic acid ethyl ester are obtained as a viscous oil.

EXAMPLE 7

Sodium 6-(4-methoxyphenyl)-2-oxo-caproate 4.5 g of 6-(4-methoxyphenyl)-2-oxo-caproic acid in 19.0 ml of 1 N sodium hydroxide solution are stirred for 15 minutes at room temperature. The mixture is filtered, washed once with diethyl ether and evaporated to dryness. The residue obtained after drying in vacuo at 30° consists of the pure sodium salt.

EXAMPLE 8

Calcium 5-(4-chlorophenyl)-2-oxo-valerate 5.3 g of 5-(4-chlorophenyl)-2-oxo-valeric acid are dissolved in 25 ml of 1 N sodium hydroxide solution and the mixture is brought to pH 8.5 with a small amount of half-concentrated hydrochloric acid. The calcium salt is precipitated by adding 2.0 g of calcium chloride dihydrate in 6 ml of water, whilst stirring, and is filtered off and dried in vacuo at 40°.

EXAMPLE 9

10,000 capsules with an active compound content of 25 mg are produced as follows:

250 g of 5-(4-chlorophenyl)-2-oxovaleric acid are dissolved in 3,000 ml of methylene chloride. The solution is mixed thoroughly with 750 g of micronised silicic acid. The mixture is evaporated to dryness and the product is then filled into size 4 hard gelatin capsules.

EXAMPLE 10

10,000 tablets with an active compound content of 30 mg are produced as follows:

300 g of 5-(4-chlorophenyl)-2-oxovaleric acid, 800 g of xylitol, 500 g of calcium phosphate, 30 mg of amorphous silicic acid and 40 g of sodium lauryl-sulphate are mixed and the mixture is sieved. This mixture is moistened with a solution of 50 g of polyvinylpyrrolidone (average molecular weight: 25,000) in 320 ml of ethanol and granulated through a sieve with a mesh width of 1.25 mm. The granules are dried at 40° and mixed with 160 g of pectin, 100 g of talc and 20 g of magnesium stearate. This mixture is pressed to 200 mg tablets with a diameter of 8 mm.

EXAMPLE 11

10,000 capsules with an active compound content of 25 mg are produced as follows:

250 g of 5-(4-methoxyphenyl)-2-oxovaleric acid, 495 g of microcrystalline cellulose and 255 g of amorphous silicic acid are mixed thoroughly and the mixture is filled into size 4 hard gelatin capsules.

PHARMACOLOGY

By virtue of their insulinotropic action, the compounds according to the invention lower the blood glucose level. In their chemical structure, they differ fundamentally from beta-cytotropic substances (for example sulphonylureas) which act on the pancreas. It proves to be particularly advantageous that the insulinotropic effect of the compounds, in contrast to commercial sulphonylureas, depends on the glucose concentration of the surrounding medium. The compounds according to the invention thus exhibit the prerequisites for a so-called "thinking antidiabetic" which stimulates insulin secretion only under conditions of hyperglycaemia, whilst under conditions of euglycaemia it does not cause any additional insulin secretion. Under these conditions, the danger of hypoglycaemia is ruled out.

In the table which follows, the compounds investigated are identified by a serial number, which is to be interpreted as follows:

| Serial No. | Name of the compound |
|---|---|
| 1 | Tolbutamide [$N^1$-n-butyl-$N^2$-(4-methylphenyl-sulphonyl)-urea] |
| 2 | 5-(4-Methoxyphenyl)-2-oxo-valeric acid |
| 3 | 6-(4-Methoxyphenyl)-2-oxo-caproic acid |
| 4 | 5-(4-Chlorophenyl)-2-oxo-valeric acid |

Table I shows investigations of insulin secretion from an isolatedly perfused rat pancreas in the course of 60 minutes, on sole addition of glucose and on addition of examples of the compounds according to the invention, to the perfusate.

TABLE I

| Insulin secretion from an isolatedly perfused rat pancreas | | | |
|---|---|---|---|
| Additives to the perfusate | | Insulin | Boosting |
| Compound No. (in [mmol/liter]) | Glucose [mmol/liter] | secretion I [ng/60 min.] | effect $I^+/I^-$ |
| — | 4 | 23 | — |
| — | 8.3 | 55 | — |
| 1(1) | 4 | 240 | 10.4 |
| 1(1) | 8.3 | 470 | 8.5 |
| 2(0.42) | 4 | 23 | 1 |
| 2(0.42) | 8.3 | 260 | 4.7 |
| 3(0.42) | 8.3 | 270 | 4.9 |
| 4(0.42) | 8.3 | 430 | 7.8 |

Re Table I:
$I^+$ = insulin secretion on addition of the test compounds and of glucose
$I^-$ = insulin secretion without addition of the test compounds but on addition of glucose Table I shows that the insulin secretion on sole addition of glucose at a concentration of 8.3 mmol/l is increased by a factor of 2.3 compared to glucose at a concentration of 4 mmol/l. The simultaneous addition of Tolbutamide increases the insulin secretion, at these glucose concentrations, by a factor of 10.4 and 8.5 respectively. In contrast, compound 2 according to the invention has no influence on the insulin secretion at a glucose concentration of 4 mmol/l, whilst at a glucose concentration of 8.3 mmol/l it causes a distinct increase of insulin secretion (to a 4.7-fold amount). An almost equally pronounced or even higher degree of increase of the insulin secretion is achieved on adding compounds 3 and 4 according to the invention.

THE PHARMACOLOGICAL PROPERTIES WERE DETERMINED IN ACCORDANCE WITH THE FOLLOWING METHOD

A. Test animals

The test animals used are male Sprague-Dawley rats (220–280 g), of the mus rattus strain, which have fasted, and are kept under standard conditions (day-night rhythm: 12 h/12 h, 23° C., 55% relative atmospheric humidity, water and standard diet: Altromin ® ad libitum). Food is withheld from the rats for 18 to 20 hours before the start of the experiment.

B. Perfusion medium

The perfusion of the rat pancreas is carried out analogously to the method described by Lenzen [Amer. J. Physiol. 236 (1979), E391–E400]. The perfusion medium used is Krebs-Henseleit buffer which contains 1 mg/ml of cattle serum albumin (Serva) and glucose in the stated amounts. The perfusion medium is constantly equilibrated with Carbogen (95% $O_2$/5% $CO_2$) in gas washbottles at 37.5° C. and pH 7.4.

C. Perfusion and operation

The rats are anaesthetised with Nembutal (0.8 ml/kg). The pancreas is isolated surgically together with the stomach, the adjoining duodenal loop and the afferent and efferent vascular system. Retrograde cannulation through the aorta is employed. All the branching vessels are ligatured so that the perfusion solution reaches the pancreas through the celiac artery, flows through it, is collected in the splenic vein and the pancreatico-duodenal vein and then passed into the portal vein. In turn, retrograde cannulation of the portal vein is employed, and here the perfusate is collected in fractions. The isolated preparation of organs is transferred to a thermostated glass vessel with an orifice at the bottom for receiving the draining capillary. The pancreas is infused at a constant flow rate of 4 ml/min. When at least 3.7 ml are being re-collected, the preparation is employed for the experiment. After a preliminary perfusion of 10 minutes in which the pancreas is flushed free from blood, perfusion is carried out for a period of 20 minutes without the test substance at the stated glucose concentration and for a period of 60 minutes at a constant test substance concentration and stated glucose concentration. In each case, the perfusate is first collected at 2 minute intervals for a period of 10 minutes, and thereafter at 5 minute intervals.

D. Insulin determination

The insulin determination is carried out by using the Radioimmunoassay of Messrs. Becton and Dickinson. This test employs guineapig antibodies against pig insulin, and uses $^{125}$I-labelled pig insulin. In this test, the free antigen is isolated by adsorption on dextran-coated active charcoal, followed by centrifugation. Very pure rat insulin from Messrs. Novo is used as the standard for the calibration curve.

The amount of insulin secreted in the course of 60 minutes is calculated from the insulin concentrations of the individual perfusate fractions. In the case of perfusion without the substance, preliminary experiments showed that the insulin secretion remains constant after 10 minutes. The efflux between minute 11 and minute 60 is then extrapolated from the efflux between minute 11 and minute 20. When this method is used, the preparation has to be subjected to the experiment for a shorter period and at the same time the control for each test is obtained within the same experiment.

We claim:

1. Substituted oxocarboxylic acids of the general formula I

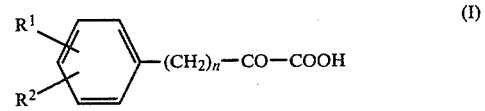

wherein $R^1$ denotes a hydrogen atom, a halogen atom, a hydroxyl group, a lower alkyl group, a lower alkoxy group or a trifluoromethyl group, $R^2$ denotes a hydrogen atom or a halogen atom and n denotes an integer from 3 to 8, excluding those wherein $R^1$ denotes a hydrogen atom or a methoxy group and $R^2$ denotes a hydrogen atom, if n denotes 3, and their salts.

2. Compounds according to claim 1, wherein n is an integer from 3 to 6, excluding those wherein $R^1$ denotes a hydrogen atom or a methoxy group and $R^2$ denotes a hydrogen atom, if n denotes 3.

3. Substituted oxocarboxylic acids according to claim 1, characterised by the general formula I*

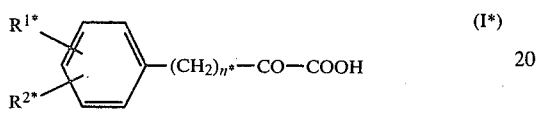

wherein $R^{1*}$ denotes a hydrogen atom, a chlorine atom, a methyl group, a methoxy group or a trifluoromethyl group, $R^{2*}$ denotes a hydrogen atom or a chlorine atom and $n^*$ denotes an integer from 3 to 6, excluding those wherein $R^{1*}$ denotes a hydrogen atom or a methoxy group and $R^{2*}$ denotes a hydrogen atom, if $n^*$ denotes 3, and their salts.

4. Substituted oxocarboxylic acids according to claim 1, characterised by the general formula I**

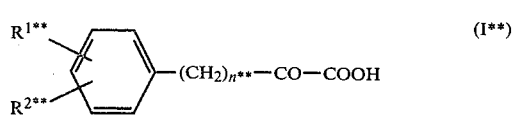

wherein $R^{1}$ and $R^{2}$ are in the meta-position or para-position to the ketocarboxylic acid radical, and $R^{1}$ denotes a hydrogen atom or a chlorine atom, $R^{2}$ denotes a chlorine atom and $n^{**}$ denotes 3 to 5, and their pharmacologically acceptable salts with inorganic or organic bases.

5. 5-(4-Methoxyphenyl)-2-oxovaleric acid and its pharmacologically acceptable salts with inorganic or organic bases, for use in the treatment of illnesses attributable to disturbances of glucose metabolism.

6. Medicaments which contain one or more of the substituted oxocarboxylic acids of the general formula I'

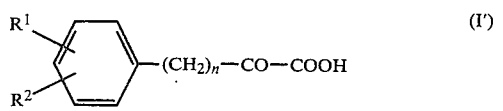

wherein $R^1$ denotes a hydrogen atom, a halogen atom, a hydroxyl group, a lower alkyl group, a lower alkoxy group or a trifluoromethyl group, $R^2$ denotes a hydrogen atom or a halogen atom and n denotes an integer from 3 to 8, and/or their pharmacologically acceptable salts with inorganic or organic bases.

7. Medicaments according to claim 6, containing substituted oxocarboxylic acids of the general formula I', wherein $R^1$ is a hydrogen atom, a chlorine atom, a methyl group, a methoxy group or a trifluoromethyl group, $R^2$ is hydrogen atom or a chlorine atom and n is an integer from 3 to 6, and/or their pharmacologically acceptable salts.

8. Medicaments according to claim 6, containing compounds according to claim 3.

9. Medicaments according to claim 6, containing compounds according to claim 4.

10. Process for the preparation of substituted oxocarboxylic acids of the general formula I

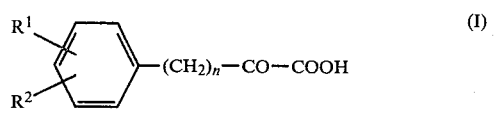

wherein $R^1$ denotes a hydrogen atom, a halogen atom, a hydroxyl groups, a lower alkyl group, a lower alkoxy group or a trifluoromethyl group, $R^2$ denotes a hydrogen atom or a halogen atom and n denotes an integer from 3 to 8, excluding those wherein $R^1$ denotes a hydrogen atom or a methoxy group and $R^2$ denotes a hydrogen atom, if n denotes 3, and their salts, characterised in that (a) an oxocarboxylic acid ester of the general formula II

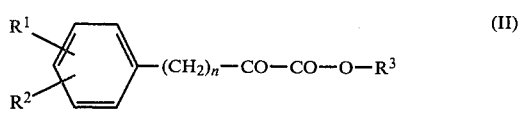

wherein $R^1$, $R^2$ and n have the abovementioned meaning and $R^3$ denotes a lower alkyl radical is solvolysed and, if appropriate, resulting acids are subsequently converted into the salts or resulting salts are subsequently converted into the acids, or (b) a diester of the general formula III

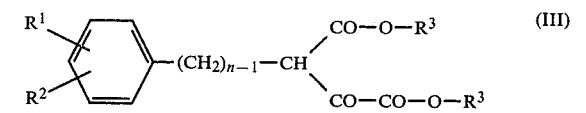

wherein $R^1$, $R^2$, $R^3$ and n have the abovementioned meaning, is solvolysed and decarboxylated, and, if appropriate, resulting acids are subsequently converted into the salts or resulting salts are subsequently converted into the acids.

11. Process according to claim 10, characterised in that oxocarboxylic acid esters II or diesters III, wherein n denotes an integer from 3 to 6, excluding those wherein $R^1$ denotes a hydrogen atom or a methoxy group and $R^2$ denotes a hydrogen atom, if n denotes 3, are employed as starting compounds.

12. Process according to claim 10 for the preparation of substituted oxocarboxylic acids of the general formula I*

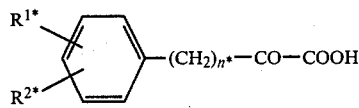 (I*)

wherein
R¹* denotes a hydrogen atom, a chlorine atom, a methyl group, a methoxy group or a trifluoromethyl group,
R²* denotes a hydrogen atom or a chlorine atom and
n* denotes an integer from 3 to 6,
excluding those wherein
R¹* denotes a hydrogen atom or a methoxy group and
R²* denotes a hydrogen atom, if
n* denotes 3,
and their salts, characterised in that (a) an oxocarboxylic acid ester of the general formula II*

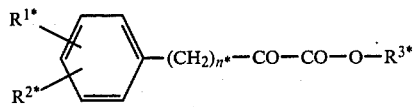 (II*)

wherein
R¹*, R²* and n* have the abovementioned meaning and
R³* denotes a lower alkyl radical,
is solvolysed and, if appropriate, resulting acids are subsequently converted into the salts or resulting salts are subsequently converted into the acids, or (b) a diester of the general formula III*

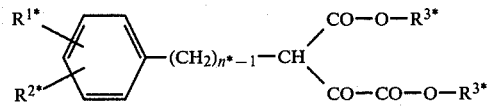 (III*)

wherein
R¹*, R²* and n* have the abovementioned meaning and
R³* denotes a lower alkyl radical,
is solvolysed and decarboxylated, and, if appropriate, resulting acids are subsequently converted into the salts or resulting salts are subsequently converted into the acids.

13. Process according to claim 10 for the preparation of substituted oxocarboxylic acids of the general formula I**

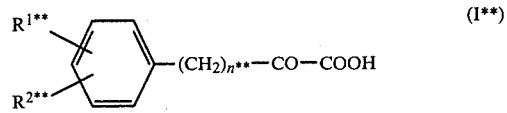 (I**)

wherein
R¹ and R² are in the meta-position or para-position to the ketocarboxylic acid radical, and
R¹** denotes a hydrogen atom or a chlorine atom,
R²** denotes a chlorine atom and
n** denotes 3 to 5,
and their salts, characterised in that (a) an oxocarboxylic acid ester of the general formula II**

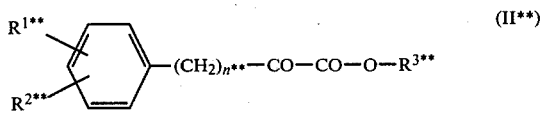 (II**)

wherein
R¹, R² and n** have the abovementioned meaning and
R³** denotes a methyl or ethyl radical,
is solvolysed and, if appropriate, resulting acids are subsequently converted into the salts or resulting salts are subsequently converted into the acids, or (b) a diester of the general formula III**

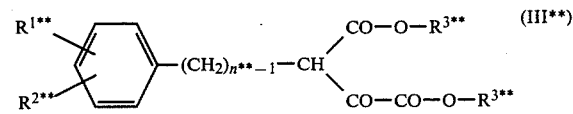 (III**)

wherein
R¹, R² and n** have the abovementioned meaning and
R³** denotes a methyl or ethyl radical,
is solvolysed and decarboxylated, and, if appropriate, resulting acids are subsequently converted into the salts or resulting salts are subsequently converted into the salts.

* * * * *

UNITED STATES PATENT AND TRADEMARK OFFICE
CERTIFICATE OF CORRECTION

PATENT NO. : 4,334,089

DATED : June 8, 1982

INVENTOR(S) : Ekkehard Kraas et al.

It is certified that error appears in the above-identified patent and that said Letters Patent is hereby corrected as shown below:

Column 1, lines 19 and 20, "ceutical active" should read -- ceutically-active --.

Column 2, line 54, "8-(4-n-butoxyphenyl)-2-oxo-octanoic" should read -- 8-[4-(n-butoxy)phenyl]-2-oxo-octanoic --.

Column 3, line 5, "formula" should read -- formulae --.

Column 4, line 26, "3" should read -- 3, --.

Column 4, line 31, "1" should read -- 1, --.

Column 4, lines 50 and 51, "abovementioned", each occurrence, should read -- previously-mentioned --.

Column 6, line 27, "abovementioned" should read --aforementioned--.

Column 6, line 41, "abovementioned" should read -- aforementioned --.

Column 6, line 43, "the salts" should read -- the salts, --.

Column 7, lines 42 and 43, "abovementioned" should read -- aforementioned --.

Column 8, line 21, "abovementioned" should read -- aforementioned --.

UNITED STATES PATENT AND TRADEMARK OFFICE
CERTIFICATE OF CORRECTION

PATENT NO. : 4,334,089
DATED : June 8, 1982
INVENTOR(S) : Ekkehard Kraas et al,

It is certified that error appears in the above-identified patent and that said Letters Patent is hereby corrected as shown below:

Column 8, line 30, after "point" insert a comma -- , --.

Column 8, line 56, after "ice-water" insert a comma -- , --.

Column 9, line 50, "vacuo," should read -- vacuo; --.

Column 9, line 51, "water" should read -- water, --.

Column 9, line 63, "hours" should read -- hours, --.

Column 9, line 65, "hours," should read -- hours; --.

Column 10, line 9, "hours" should read -- hours, --.

Column 10, line 58, "toluene," should read -- toluene; --.

Column 10, line 64, after "ethanol" insert a comma -- , --.

Column 10, line 68, after "concentrated" insert a comma -- , --.

Column 11, line 2, "organic phases collected" should read -- collected organic phases --.

Column 11, line 61, ", and worked up," should read --and worked up-

Column 11, line 67, after "trichloride" insert a comma -- , --.

Column 12, line 3, delete the comma " , ".

Column 13, line 16, "n-butyl" should read -- (n-butyl) --.

UNITED STATES PATENT AND TRADEMARK OFFICE
CERTIFICATE OF CORRECTION

PATENT NO. : 4,334,089

DATED : June 8, 1982

INVENTOR(S) : Ekkehard Kraas et al.

It is certified that error appears in the above-identified patent and that said Letters Patent is hereby corrected as shown below:

Column 13, line 48, after "8.5" insert a comma -- , --.

Column 13, line 66, "R" should read -- -- ⓡ --.

Column 14, line 56, after "period" insert a comma -- , --.

Cancel claims 1 to 13 and add the following claims:

1. 1. A compound of the formula

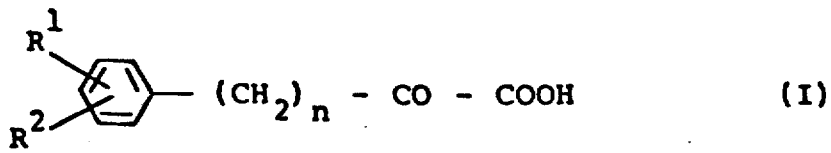

wherein $R^1$ is hydrogen (-H), halo, hydroxy, lower alkyl, lower alkoxy or trifluoromethyl;

$R^2$ is hydrogen (-H) or halo, but is halo when $R^1$ is hydrogen (-H) or methoxy and n is 3; and n is an integer from 3 to 8;

or a salt thereof.

2. A compound according to claim 1 wherein n is an integer from 3 to 6.

UNITED STATES PATENT AND TRADEMARK OFFICE
CERTIFICATE OF CORRECTION

PATENT NO. : 4,334,089
DATED : June 8, 1982
INVENTOR(S) : Ekkehard Kraas et al.

It is certified that error appears in the above-identified patent and that said Letters Patent is hereby corrected as shown below:

3. A compound according to claim 2 wherein $R^1$ is a hydrogen atom (-H), chloro, methyl, methoxy or trifluoromethyl and R is a hydrogen atom (-H) or halo, or a salt thereof.

4. A compound according to claim 1 wherein $R^1$ is a hydrogen atom (-H) or chloro, $R^2$ is chloro, each of $R^1$ and $R^2$ is in a position meta or para to the keto-
carboxylic acid radical, and n is one of the integers, 3, 4 and 5, or a pharmacologically-acceptable salt thereof.

5. A method for prophylaxis or treatment of illness attributable to disturbance of glucose metabolism which comprises administering to a person subject to or afflicted with such illness an effective amount of 5-(4-methoxyphenyl)-2-oxovaleric acid or a pharmacologically-acceptable salt thereof.

6. A method for prophylaxis or treatment of illness attributable to disturbance of glucose metabolism which

UNITED STATES PATENT AND TRADEMARK OFFICE
CERTIFICATE OF CORRECTION

PATENT NO. : 4,334,089
DATED : June 8, 1982
INVENTOR(S) : Ekkehard Kraas et al.

It is certified that error appears in the above-identified patent and that said Letters Patent is hereby corrected as shown below:

comprises administering to a person subject to or afflicted with such illness an effective amount of a compound of the formula

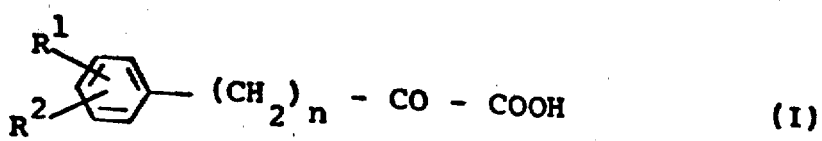

wherein $R^1$ is a hydrogen atom (-H), halo, hydroxy, lower alkyl, lower alkoxy or trifluoromethyl;

$R^2$ is a hydrogen atom (-H) or halo; and n is an integer from 3 to 8, inclusive;

or of a pharmacologically-acceptable salt thereof.

7. A medicament composition comprising pharmaceutical excipient and from 1 to 95 percent by weight of a least one compound of the formula

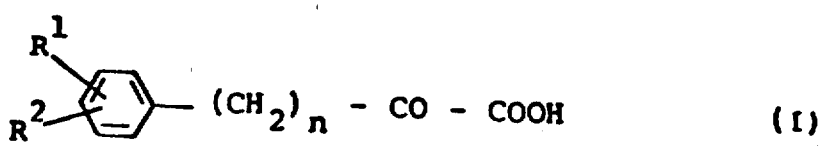

UNITED STATES PATENT AND TRADEMARK OFFICE
CERTIFICATE OF CORRECTION

PATENT NO. : 4,334,089
DATED : June 8, 1982
INVENTOR(S) : Ekkehard Kraas et al.

It is certified that error appears in the above-identified patent and that said Letters Patent is hereby corrected as shown below:

wherein $R^1$ is a hydrogen atom (-H), halo, hydroxy, lower alkyl, lower alkoxy or trifluoromethyl;

$R^2$ is a hydrogen atom (-H) or halo; and n is an integer from 3 to 8, inclusive;

or of a pharmacologically-acceptable salt thereof.

8. A medicament composition according to claim 7 wherein $R^1$ is a hydrogen atom (-H), chloro, methyl, methoxy or trifluoromethyl, $R^2$ is a hydrogen atom (-H) or chloro, and n is an integer from 3 to 6, inclusive;

or a pharmacologically-acceptable salt thereof.

9. A medicament composition comprising pharmaceutical excipient and from 1 to 95 percent by weight of at least one acid according to claim 3 or a pharmacologically-acceptable salt thereof.

UNITED STATES PATENT AND TRADEMARK OFFICE
CERTIFICATE OF CORRECTION

PATENT NO. : 4,334,089
DATED : June 8, 1982
INVENTOR(S) : Ekkehard Kraas et al.

It is certified that error appears in the above-identified patent and that said Letters Patent is hereby corrected as shown below:

10. A medicament composition comprising pharmaceutical excipient and from 1 to 95 percent by weight of at least one acid according to claim 4 or a pharmacologically-acceptable salt thereof.

On the Title Page, "13 Claims, No Drawings" should read -- 10 Claims, No Drawings --.

Signed and Sealed this

Twenty-eighth Day of December 1982

[SEAL]

Attest:

Attesting Officer

GERALD J. MOSSINGHOFF

Commissioner of Patents and Trademarks

UNITED STATES PATENT AND TRADEMARK OFFICE
CERTIFICATE OF CORRECTION

PATENT NO. : 4,334,089

DATED : June 8, 1982

INVENTOR(S) : Ekkehard KRAAS and Horst WOLF

It is certified that error appears in the above-identified patent and that said Letters Patent are hereby corrected as shown below:

Column 6, line 54, "1971" should read --*1971*--; lines 56 and 57, "1978" (each occurrence) should read --*1978*--. Column 9, line 45, "1979" should read --*1979*--. Column 10, line 33, "caproci" should read --caproic--. Column 14, line 20, "passed" should read --passes--.

Signed and Sealed this

Fifth Day of April 1983

[SEAL]

Attest:

GERALD J. MOSSINGHOFF

Attesting Officer     Commissioner of Patents and Trademarks